United States Patent [19]

Garabedian

[11] Plant 5,047

[45] May 3, 1983

[54] GRAPEVINE

[76] Inventor: John M. Garabedian, P.O. Box 7883, Fresno, Calif. 93747

[21] Appl. No.: 314,704

[22] Filed: Oct. 26, 1981

[51] Int. Cl.[3] ..... A01H 5/03

[52] U.S. Cl. ..... Plt./47

[58] Field of Search ..... Plt./47

*Primary Examiner*—Robert E. Bagwill

*Attorney, Agent, or Firm*—Huebner & Worrel

[57] ABSTRACT

A grapevine generally resembling the Thompson Seedless Grapevine (unpatented), but distinguished by bearing, without girdling or application of a growth regulator, grapes of a size borne by the Thompson Seedless variety only when so treated and distinguished by bearing bunches of grapes which are substantially free from shatter in cold storage and when subsequently displayed for sale.

1 Drawing Figure

The present invention relates to a new and distinct variety of grapevine and more particularly to a seedless variety characterized as to novelty by resistance to shattering and improved size.

BACKGROUND OF THE NEW VARIETY

The Thompson Seedless or Sultana variety (unpatented) grapevine is one of the most extensively planted varieties for the production of table grapes, grapes of this variety also being extensively utilized for producing raisins and wine. Despite its extensive planting, the Thompson Seedless variety has two serious deficiencies when utilized for table grape production. The bunches of grapes from this variety have a severe tendency to shatter, that is the individual berries become detached from their respective bunches. This tendency is particularly pronounced when the Thompson Seedless grapes are removed from cold storage for retail sale, with the result that the bunches have a short shelf life and soon become unattractive. The other serious deficiency of the Thompson Seedless variety of grapevine for table use is that the grapes are objectionably small unless the vines are girdled and/or sprayed with a growth regulator, typically gibberellin, the expense of extra labor and/or growth regulator being in the order of $1,000 per acre at the present time.

It is apparent that a new variety of grapevine, which bears grapes having the desirable characteristics of grapes of the Thompson Seedless variety from vines which have been girdled and/or treated with gibberellin, would be highly advantageous from the standpoint of growing expense and that such a new variety would be additionally advantageous from the marketing standpoint if bunches of grapes therefrom were not subject to shattering prior to and after display for sale.

ORIGIN AND ASEXUAL REPRODUCTION OF THE NEW VARIETY

In the interest of developing new and improved varieties of grapevines, blossoms of grapevines of the Almeria variety (unpatented) growing on a ranch, which is owned by me and is located at 12470 East Church Ave. near the City of Sanger, in the County of Fresno and in the State of California, were hand-pollinated at my direction with pollen from another variety of grapevine, believed to be of the Thompson Seedless variety. The seeds were removed from the resultant grapes, and from other grapes resulting from such pollination, and grown at my designated ranch. When such seedlings produced grapes, the subject variety was discovered by me growing among numerous seedlings resulting from such pollination and was recognized to have novel characteristics. The subject variety was selected by me and asexually reproduced by budding under my supervision on my designated ranch and the fruit and vine characteristics resulting from such propagation were observed to be identical to those of the seedling which produced the scions used in such asexual reproduction.

SUMMARY OF THE NEW VARIETY

The subject variety of grapevine is generally characterized by its bearing of light-greenish, elongated, substantially seedless, grapes resembling those of the Thompson Seedless (unpatented) variety of grapevine and ripening therewith. The grapes of the new variety of grapevine, without girdling and/or application of a growth regulator thereto, are of the size attained by grapes of the Thompson Seedless variety of grapevine grown in the same vicinity when vines of the latter variety have been girdled and/or treated with gibberellin.

The new variety is further distinguished from and is superior to the Thompson Seedless (unpatented) variety in that bunches of grapes from the new variety are highly resistant to shattering even without being girdled and/or treated with gibberellin. In fact, the new variety is superior from the standpoint of shattering to any other variety known to me, bunches of grapes picked on Aug. 22, 1980 being substantially free from shattering two months later when held under refrigeration as compared with the Thompson Seedless variety which shatters in a week or two under similar refrigeration.

BRIEF DESCRIPTION OF THE DRAWINGS

The accompanying drawing is a color photograph of two bunches of mature grapes of the subject variety, together with representative leaves.

DETAILED DESCRIPTION

Referring more specifically to the pomological details of this new and distinct variety of grapevine, the following has been observed under the ecological conditions prevailing at the above-designated ranch. The color code plate identifications are by reference to the Maerz and Paul *Dictionary of Color,* Second Edition, McGraw-Hill Book Co., Inc. 1950, common description color names also being used.

VINE

Generally: Horizontal and open in configuration; vigorous; hardy; productive, a typical young vine having sixteen clusters.

Trunk: Small and slender, bark adherent and slightly shreddy.

Canes: Numerous and mostly straight;

*Thickness.*—Mostly medium with some slender.

*Length.*—1 to 102 inches (2.5 to 260 cm.), average 39.9 inches (104 cm.).

*Color.*—Plate 13-I-8 (Aztec).

*Nodes.*—Very slightly enlarged.

*Internodes.*—Mostly medium in length with faint striations of color.

*Tendrils.*—Intermittent and smooth, mostly trifurcated, medium in length and thickness.

Flowers: Fertile; stamens upright and reflexed; early blooming, first bloom about June 5 and full bloom about June 13.

Leaves: Glabrous;

*Size.*—Medium, width times length factor 30.7 sq. in. (198 sq. cm.).

*Form.*—Cordate; five lobes with terminal lobe obtuse; petiolar sinus medium depth and overlapping; basal sinus and each lateral sinus medium in width and medium to shallow in depth.

*Margin.*—Dentate with teeth of medium width and depth, 50 to 78 per leaf, average 58.

*Upper surface.*—Medium smoothness; medium to dark green, Plate 23-H-7 (approximately Mt. Vernon Green, Plate 23-J-8).

*Lower surface.*—Pale green, Plate 21-L-1 (approximately Leek Green, Plate 22-J-5).

FRUIT

Maturity: Mid-season, Aug. 22 in 1980.

Form: Mostly elipsoidal and elongated.

Size: Mostly large, many medium; length 1 3/16 to 1¾ inches (30 to 44.5 mm.).

Skin; Thin; medium tenderness; separates from pulp;

*Color.*—Light green yellow on Oct. 23, 1980, with thick bloom; some berries with small lenticel spots.

Flesh: Translucent; white-greenish in color; meaty; tender; medium juiciness with clear juice.

Seeds: Vestigal only; average number 1.1 per berry; very small and tender and not noticeable on eating.

Cluster: Medium in size, average weight 19.9 oz. (564 g.); medium length and broadness; loose;

*Form.*—Tapering; short conical to conical; double-shouldered, a few single.

Peduncle: Tough;

*Length.*—Mostly long, many medium, 1 to 2 inches (25–50 mm.).

*Thickness.*—Medium, greater on larger bunches.

Pedicel:

*Length.*—Mostly medium, average 3/16 to ⅜ inches (5 to 10 mm.).

*Thickness.*—Thick, 1/16 inch (1½ mm.).

Keeping, shipping, and eating quality: (Based on fruit harvested Oct. 23, 1980 and overripe)

*Keeping quality.*—Very good.

*Shipping quality.*—Very good.

*Freedom from shatter.*—Very good, none shattered.

*Eating quality.*—Very good with flesh firm, sweet, and good tasting; refractometer test, 22% solids; sugar to acid ratio, 3.8 (very low acid).

Uses: Primarily for fresh table use because of superior keeping and shipping qualities, but also suitable for raisin and wine production.

Although the new variety of grapevine possesses the stated characteristics under the growing conditions in Fresno County, Calif. in the central part of the San Joaquin Valley, it is to be understood that variations of the usual magnitude incident to growing conditions, fertilization, pruning, and pest control are to be expected.

Having thus described and illustrated my new variety of grapevine, I claim:

1. A new and distinct variety of grapevine, substantially as illustrated and described, characterized by its general resemblance to the Thompson Seedless grapevine (unpatented) in bearing elongated, seedless, light green grapes, but being distinguished therefrom and characterized as to novelty by bearing grapes which, without girdling or the application of a growth regulator, are of a size only attained in the Thompson Seedless variety by girdling and/or such application and which are borne in bunches which are substantially free from shattering even when held for a protracted period.

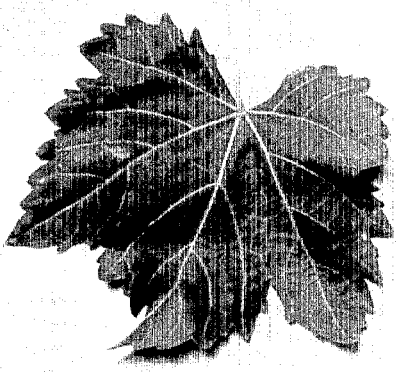
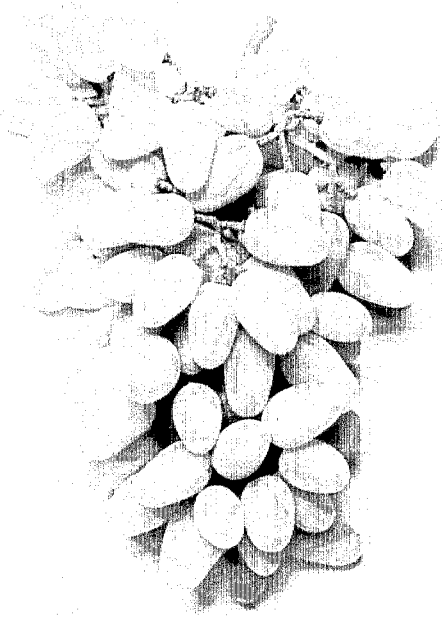
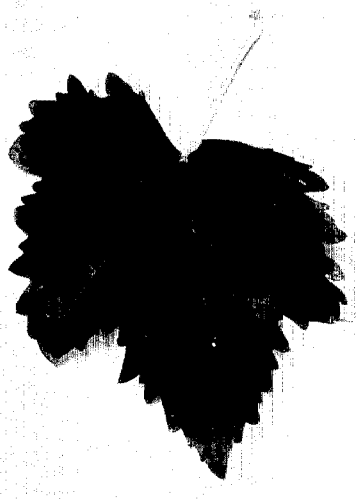
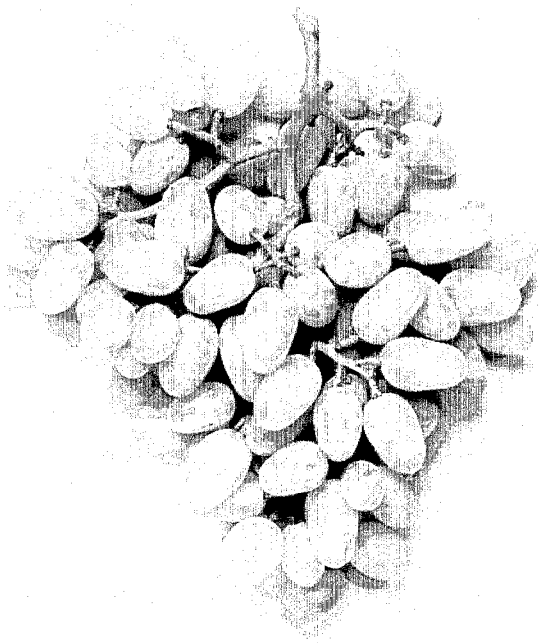

* * * * *